(12) United States Patent
Burger et al.

(10) Patent No.: US 8,715,275 B2
(45) Date of Patent: May 6, 2014

(54) PAIN MANAGEMENT USING CRYOGENIC REMODELING

(75) Inventors: Keith Burger, San Francisco, CA (US); Lisa Elkins, Woodside, CA (US); Ronald Williams, Menlo Park, CA (US)

(73) Assignee: MyoScience, Inc., Redwood City, CA (US)

( * ) Notice: Subject to any disclaimer, the term of this patent is extended or adjusted under 35 U.S.C. 154(b) by 0 days.

(21) Appl. No.: 13/615,059

(22) Filed: Sep. 13, 2012

(65) Prior Publication Data

US 2013/0218148 A1    Aug. 22, 2013

Related U.S. Application Data

(63) Continuation of application No. 12/271,013, filed on Nov. 14, 2008, now Pat. No. 8,298,216.

(60) Provisional application No. 60/987,992, filed on Nov. 14, 2007.

(51) Int. Cl.
*A61B 18/18* (2006.01)

(52) U.S. Cl.
USPC .................. 606/22; 606/20; 606/21

(58) Field of Classification Search
CPC ........................................................ A61B 18/18
USPC ....................................................... 606/20–23
See application file for complete search history.

(56) References Cited

U.S. PATENT DOCUMENTS

| | | | |
|---|---|---|---|
| 2,319,542 A | 5/1943 | Hall | |
| 2,672,032 A | 3/1964 | Towse | |
| 3,226,492 A | 12/1965 | Steinberg | |
| 3,343,544 A | 9/1967 | Dunn et al. | |
| 3,507,283 A | 4/1970 | Thomas, Jr. | |
| 3,532,094 A | 10/1970 | Stahl | |

(Continued)

FOREIGN PATENT DOCUMENTS

| | | |
|---|---|---|
| CA | 0 643 474 | 9/2007 |
| EP | 0 043 447 A2 | 6/1981 |

(Continued)

OTHER PUBLICATIONS

Advanced Cosmetic Intervention, Inc. [webpage], retrieved from the Internet: <<http://www.acisurgery.com>>, copyright 2007, 1 page.

(Continued)

*Primary Examiner* — Nicholas Lucchesi
*Assistant Examiner* — Gerald Landry, II
(74) *Attorney, Agent, or Firm* — Kilpatrick Townsend & Stockton LLP

(57) ABSTRACT

Medical devices, systems, and methods for pain management and other applications may apply cooling with at least one probe inserted through an exposed skin surface of skin. The cooling may remodel one or more target tissues so as to effect a desired change in composition of the target tissue and/or a change in its behavior, often to interfere with transmission of pain signals along sensory nerves. Alternative embodiments may interfere with the function of motor nerves, the function of contractile muscles, and/or some other tissue included in the contractile function chain so as to inhibit muscle contraction and thereby alleviate associated pain. In some embodiments, other sources of pain such as components of the spine (optionally including herniated disks) may be treated.

30 Claims, 8 Drawing Sheets

(56) References Cited

U.S. PATENT DOCUMENTS

| | | |
|---|---|---|
| 3,664,344 A | 5/1972 | Bryne |
| 3,795,245 A | 3/1974 | Allen, Jr. et al. |
| 3,830,239 A | 8/1974 | Stumpf et al. |
| 3,886,945 A | 6/1975 | Stumpf et al. |
| 3,889,681 A | 6/1975 | Waller et al. |
| 3,951,152 A | 4/1976 | Crandell et al. |
| 3,993,075 A | 11/1976 | Lisenbee et al. |
| 4,140,109 A | 2/1979 | Savic et al. |
| 4,207,897 A | 6/1980 | Lloyd et al. |
| 4,306,568 A | 12/1981 | Torre |
| 4,376,376 A | 3/1983 | Gregory |
| 4,404,862 A | 9/1983 | Harris, Sr. |
| 4,524,771 A | 6/1985 | McGregor et al. |
| 4,758,217 A | 7/1988 | Gueret |
| 4,802,475 A | 2/1989 | Weshahy |
| 4,946,460 A | 8/1990 | Merry et al. |
| 5,200,170 A | 4/1993 | McDow |
| 5,334,181 A | 8/1994 | Rubinsky et al. |
| 5,571,147 A | 11/1996 | Sluijter et al. |
| 5,647,868 A | 7/1997 | Chinn |
| 5,755,753 A | 5/1998 | Knowlton |
| 5,814,040 A | 9/1998 | Nelson et al. |
| 5,899,897 A | 5/1999 | Rabin et al. |
| 5,916,212 A | 6/1999 | Baust et al. |
| 5,976,505 A | 11/1999 | Henderson |
| 6,003,539 A | 12/1999 | Yoshihara |
| 6,032,675 A | 3/2000 | Rubinsky |
| 6,039,730 A | 3/2000 | Rabin et al. |
| 6,041,787 A | 3/2000 | Rubinsky |
| 6,139,545 A | 10/2000 | Utley et al. |
| 6,141,985 A | 11/2000 | Cluzeau et al. |
| 6,182,666 B1 | 2/2001 | Dobak, III |
| 6,196,839 B1 | 3/2001 | Ross |
| 6,277,099 B1 | 8/2001 | Strowe et al. |
| 6,277,116 B1 | 8/2001 | Utely et al. |
| 6,371,943 B1 * | 4/2002 | Racz et al. ............. 604/274 |
| 6,432,102 B2 | 8/2002 | Joye et al. |
| 6,494,844 B1 | 12/2002 | Van Bladel et al. |
| 6,503,246 B1 | 1/2003 | Har-Shai et al. |
| 6,506,796 B1 | 1/2003 | Fesus et al. |
| 6,546,935 B2 | 4/2003 | Hooven |
| 6,551,309 B1 | 4/2003 | LePivert |
| 6,562,030 B1 | 5/2003 | Abboud et al. |
| 6,648,880 B2 | 11/2003 | Chauvet et al. |
| 6,669,688 B2 | 12/2003 | Svaasand et al. |
| 6,672,095 B1 | 1/2004 | Luo |
| 6,706,037 B2 | 3/2004 | Zvuloni et al. |
| 6,723,092 B2 | 4/2004 | Brown et al. |
| 6,749,624 B2 | 6/2004 | Knowlton |
| 6,761,715 B2 | 7/2004 | Carroll |
| 6,764,493 B1 | 7/2004 | Weber et al. |
| 6,786,902 B1 | 9/2004 | Rabin et al. |
| 6,789,545 B2 | 9/2004 | Littrup et al. |
| 6,858,025 B2 | 2/2005 | Maurice |
| 6,905,492 B2 | 6/2005 | Zvuloni et al. |
| 6,960,208 B2 | 11/2005 | Bourne et al. |
| 7,081,111 B2 | 7/2006 | Svaasand et al. |
| 7,083,612 B2 | 8/2006 | Littrup et al. |
| 7,195,616 B2 | 3/2007 | Diller et al. |
| 7,217,939 B2 | 5/2007 | Johansson et al. |
| 7,250,046 B1 | 7/2007 | Fallat |
| 7,311,672 B2 | 12/2007 | Van Bladel et al. |
| 7,367,341 B2 | 5/2008 | Anderson et al. |
| 7,402,140 B2 | 7/2008 | Spero et al. |
| 7,422,586 B2 | 9/2008 | Morris et al. |
| 7,578,819 B2 * | 8/2009 | Bleich et al. ............. 606/53 |
| 8,298,216 B2 | 10/2012 | Burger et al. |
| 2002/0013602 A1 | 1/2002 | Huttner |
| 2002/0045434 A1 | 4/2002 | Masoian et al. |
| 2002/0068929 A1 | 6/2002 | Zvuloni |
| 2002/0183731 A1 | 12/2002 | Holland et al. |
| 2002/0193778 A1 | 12/2002 | Alchas et al. |
| 2003/0036752 A1 | 2/2003 | Joye et al. |
| 2003/0109912 A1 | 6/2003 | Joye et al. |
| 2003/0181896 A1 | 9/2003 | Zvuloni et al. |
| 2004/0122482 A1 | 6/2004 | Tung et al. |
| 2004/0162551 A1 | 8/2004 | Brown et al. |
| 2004/0167505 A1 | 8/2004 | Joye et al. |
| 2004/0191229 A1 | 9/2004 | Link et al. |
| 2004/0204705 A1 | 10/2004 | Lafontaine |
| 2004/0210212 A1 | 10/2004 | Maurice |
| 2004/0215178 A1 * | 10/2004 | Maurice .................. 606/22 |
| 2004/0215294 A1 | 10/2004 | Littrup et al. |
| 2004/0220648 A1 * | 11/2004 | Carroll .................. 607/105 |
| 2004/0225276 A1 | 11/2004 | Burgess |
| 2004/0243116 A1 | 12/2004 | Joye et al. |
| 2005/0004563 A1 * | 1/2005 | Racz et al. ................ 606/34 |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks |
| 2005/0209565 A1 | 9/2005 | Yuzhakov et al. |
| 2005/0209587 A1 | 9/2005 | Joye et al. |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0084962 A1 | 4/2006 | Joye et al. |
| 2006/0129142 A1 | 6/2006 | Reynolds |
| 2006/0189968 A1 | 8/2006 | Howlett et al. |
| 2006/0200117 A1 * | 9/2006 | Hermans .................. 606/25 |
| 2006/0212028 A1 | 9/2006 | Joye et al. |
| 2006/0223052 A1 | 10/2006 | MacDonald et al. |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1 | 6/2007 | Elkins et al. |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0171334 A1 * | 7/2009 | Elkins et al. ............. 606/21 |
| 2009/0264876 A1 * | 10/2009 | Roy et al. ................ 606/21 |

FOREIGN PATENT DOCUMENTS

| | | |
|---|---|---|
| EP | 0 777123 A2 | 6/1997 |
| EP | 1 074 273 A2 | 2/2001 |
| EP | 1 377 327 B1 | 9/2007 |
| GB | 1 360 353 A | 7/1974 |
| GB | 1402632 | 8/1975 |
| JP | 10-014656 | 1/1998 |
| JP | 2006-130055 | 5/2006 |
| WO | 97/49344 | 12/1997 |
| WO | 01/97702 | 12/2001 |
| WO | 02/092153 | 11/2002 |
| WO | 2004/039440 A1 | 5/2004 |
| WO | 2004/045434 | 6/2004 |
| WO | 2004/089460 | 10/2004 |
| WO | 2005/000106 | 1/2005 |
| WO | 2005/079321 A2 | 9/2005 |
| WO | 2006/012128 | 2/2006 |
| WO | 2006/023348 | 3/2006 |
| WO | 2006/125835 | 11/2006 |
| WO | 2007/037326 | 4/2007 |

(56) References Cited

FOREIGN PATENT DOCUMENTS

| WO | 2007/089603 | 8/2007 |
|---|---|---|
| WO | 2007/135629 | 11/2007 |
| WO | 2009/026471 | 2/2009 |

OTHER PUBLICATIONS

Cryopen, LLC [Press Release], "GyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.

Cryopen, LLC., [webpage], retrieved from the Internet: <<http://cryopen.com/>>, copyright 2006-2008, 2 pages total.

Cryosurgical Concepts, Inc., [webpage] "CryoProbeTM", retrieved from the Internet: << http://www.cryo-surgical.com//>> on Feb. 8, 2008, 2 pages total.

Har-Shai et al., "Effect of skin surface temperature on skin pigmentation during contact and intralesional cryosurgery of hypertrophic scars and Kleoids," Journal of the European Academy of Dermatology and Venereology 21 (2), 191-198.

One Med Group, LLC., [webpage] "CryoProbeTM", retrieved from the Internet: << http://www.onemedgroup.com/>> on Feb. 8, 2008, 2 pages total.

Utley et al., "Radiofrequency Ablation of the Nerve to the Corrugator Muscle for the Elimination of Glabellar Furrowing," Arch. Facial Plastic Surgery 1: 46-48, 1999.

International Search Report and Written Opinion of PCT Application No. PCT/US2008/083668, mailed on Feb. 27, 2009, 13 pages total.

Yang et al., "Apoptosis induced by cryo-injury in human colorectal cancer cells is associated with mitochondrial dysfunction.," Int J Cancer. Jan. 20, 2003;103(3):360-369.

Dasiou-Plankida, "Fat injections for facial rejuvenation: 17 years experience in 1720 patients," Journal of Cosmetic Dermatology, Oct. 22, 2004; 2(3-4): 119-125.

Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.

Magalov et al., "Isothermal volume contours generated in a freezing gel by embedded cryo-needles with applications to cryo-surgery," Cryobiology, Oct. 2007; 55(2):127-137.

Rewcastle et al., "A model for the time dependent three-dimensional thermal distribution within iceballs surrounding multiple cryoprobes," Med Phys. Jun. 2001;28(6):1125-37.

Metrum CryoFlex, Cryosurgery probes and accessories catalogue, 2009, 25 pages.

Metrum CryoFlex, Cryoablation in pain management brochure, 2012, 5 pages.

* cited by examiner

Needle inserted to interspinal ligament

Constant pressure on syringe plunger

Saline injected into epidural space

PAIN MANAGEMENT USING CRYOGENIC REMODELING

CROSS-REFERENCES TO RELATED

The present application is a Continuation of Ser. No. 12/271,013 filed Nov. 14, 2008 (Allowed), which claims the benefit under 35 USC 119(e) of U.S. Provisional Application No. 60/987,992 filed Nov. 14, 2007; the full disclosures, each of which are incorporated herein by reference in their entirety for all purposes.

BACKGROUND OF THE INVENTION

The present invention is directed to medical devices, systems, and methods, particularly for those which employ cold for treatment of pain in a patient. Embodiments of the invention include cryogenic cooling needles that can be advanced through skin or other tissues to inhibit neural transmission of pain signals. Other embodiments may inhibit muscle spasm induced pain. The cooling may be applied so that the pain-inhibiting remodeling relies on mechanisms other than ablation.

Therapeutic treatment of chronic or acute pain is among the most common reasons patients seek medical care. Chronic pain may be particularly disabling, and the cumulative economic impact of chronic pain is huge. A large portion of the population that is over the age of 65 may suffer from any of a variety of health issues which can predispose them to chronic or acute pain. An even greater portion of the nursing home population may suffer from chronic pain.

Current treatments for chronic pain may include pharmaceutical analgesics and electrical neurostimulation. While both these techniques may provide some level of relief, they can have significant drawbacks. For example, pharmaceuticals may have a wide range of systemic side effects, including gastrointestinal bleeding, interactions with other drugs, and the like. Opiod analgesics can be addictive, and may also of themselves be debilitating. The analgesic effects provided by pharmaceuticals may be relatively transient, making them cost-prohibitive for the aging population that suffers from chronic pain. While neurostimulators may be useful for specific applications, they generally involve surgical implantation, an expensive which carries its own risks, side effects, contraindications, on-going maintenance issues, and the like.

Neurolysis is a technique for treating pain in which a nerve is damaged so that it can no longer transmit pain signals. The use of neurotoxins (such as botulinum toxin or BOTOX®) for neurolysis has received some support. Unfortunately, significant volumes of toxins may be used on a regular basis for effective neurolysis, and such use of toxins can have significant disadvantages. Alternative neurolysis techniques may involve the use of thermal injury to the nerves via the application of radiofrequency ("RF") energy to achieve ablation, cryoablation, or the like. While several of these alternative neurolysis approaches may avoid systemic effects and/or prevent damage, additional improvements to neurolysis techniques would be desirable.

In general, it would be advantageous to provide improved devices, systems, and methods for management of chronic and/or acute pain. Such improved techniques may avoid or decrease the systemic effects of toxin-based neurolysis and pharmaceutical approaches, while decreasing the invasiveness and/or collateral tissue damage of at least some known pain treatment techniques.

BRIEF SUMMARY OF THE INVENTION

The present invention generally provides improved medical devices, systems, and methods for treatment of pain and other applications. Embodiments of the present invention may apply cooling with at least one probe inserted through an exposed skin surface (and/or other tissue overlying a nerve) of a patient. The cooling may remodel one or more target tissues so as to effect a desired change in composition of the target tissue and/or a change in its behavior. Exemplary embodiments will interfere with transmission of pain signals along sensory nerves. Alternative embodiments may interfere with the function of motor nerves, the function of contractile muscles, and/or some other tissue included in a contractile function chain so as to inhibit muscle contraction and thereby alleviate chronic or acute pain related to muscle activity. In some embodiments, other sources of pain such as components of the spine (optionally including herniated disks) may be treated.

In a first aspect, the invention provides a method for treating pain associated with a nerve of a patient. The nerve underlies a tissue. The method comprises manually manipulating a body of a treatment apparatus with a hand. The body supports a needle, and the body is manipulated so as to penetrate a sharpened distal end of the needle into the tissue to thermally couple the needle with the nerve. The body supports a cooling fluid source, and cooling fluid is transmitted from the source to the needle so that the fluid cools the needle and the needle cools the nerve sufficiently that pain is inhibited.

The cooling fluid may cool the needle to a needle temperature in a target temperature range. The target temperature range may be determined in response to a desired duration of pain inhibition. The needle temperature may, for example, be sufficiently warm to inhibit ablation of the nerve. The desired duration may optionally be permanent, and the needle temperature may be suitable to induce apoptosis of the nerve. Apoptosis-inducing treatments will not necessarily be permanent, as repair mechanisms may still limit the pain inhibiting duration. Nonetheless, apoptosis may enhance pain relief duration (for example, to provide pain relief lasting a plurality of months) and/or the duration of other effects of the cooling when compared to alternative treatment regimes. The desired duration may alternatively be less than permanent, for example, with the needle temperature being in a tissue stunning temperature range so that the nerve is capable of transmitting pain signals after the tissue warms. Optionally, the needle may be inserted in or adjacent to an epidural space near a spinal channel. By thermally coupling the needle to nerves within the spinal channel (and/or peripheral nerves branching from the spinal channel) cooling of the needle may be used to inhibit pain transmission into or via the spinal channel.

In the exemplary embodiment, the body comprises a self-contained, hand-held body so that no power, cooling fluid, or other material need be transmitted from a stationary structure along a flexible tether during treatment. At least a portion of the cooling may optionally be performed through an electrically insulating surface of the needle, with the needle often also having an electrically conductive surface. Measurement of the nerve may be provided by an electromyographic ("EMG") system coupled to the electrically conductive surface of the needle. The needle will often be used to penetrate a skin surface of the patient overlying the nerve, and visible scar formation along the skin surface may be inhibited by limiting cooling along the needle proximally of the nerve. In some embodiments, a plurality of cooling cycles may be used to treat the nerve, with the probe being warmed or warm fluid being injected to speed thawing between the cooling cycles. In many embodiments, a needle may be detached from the body and another needle mounted in its place. The other needle is then used to cool tissue with cooling fluid from the cooling source. The body (and cooling fluid source) can be disposed of after treating only the one patient. Refilling of the cooling fluid source can be inhibited so as to prevent use of the system with another patient, for example, by configuring the cooling fluid path to release the lost gases through appropriately shaped vents rather than refill couplers or the like.

In another aspect, the invention provides a system for treating pain of a patient. The pain is associated with a nerve of the patient, and the nerve underlies a tissue. A system comprises a body having a handle and a needle that is supported by the handle. The needle has a proximal end adjacent the body and a distal end. The distal end is sharpened for penetrating distally into the tissue to thermally couple the needle with the nerve using manipulation of the handle. The cooling fluid source is mounted to the body and is supported by the handle. The cooling fluid source is coupled to the needle along a fluid path. A fluid flow control system is coupled to the fluid path so that the fluid cools the needle and the needle effects cooling of the nerve to inhibit the pain.

In another aspect, the invention provides a system for treating pain of a patient. The pain is associated with a nerve underlying a tissue of the patient. The system comprises a body having a handle and a needle that is supported by the handle. The needle has a proximal end adjacent the body and a distal end with a lumen extending between the proximal and distal ends. The distal end is sharpened for penetrating distally into the tissue so as to thermally couple the lumen with the nerve. The needle has a 16-gauge needle size or less. A cooling fluid source is coupled to the lumen of the needle by a fluid path, and a fluid flow control system coupled to the fluid path is configured to introduce cool fluid from the cooling fluid source, so that the vaporization of the fluid within the lumen effects cooling of the nerve to inhibit the pain.

The needle will often have a 22-gauge needle size or less, preferably having a 26-gauge needle size or less. Multiple needles may optionally be provided to enhance and/or widen a treatment volume, such as by providing two (or alternatively more than two) parallel and laterally offset needles. The fluid flow control system may comprise a length of silica tubing disposed along the fluid flow control path between the cooling fluid source and the lumen. Such tubing may have a small, very consistent inner diameter that helps meter the fluid flow, allowing the temperature to be effectively controlled by a simple pressure control valve disposed between the lumen and an exhaust.

In yet another aspect, the invention provides a method for treating pain associated with a component of a spine of a patient. The method comprises denervating at least a portion of the component, the at least a portion implicated in the pain. The component may comprise, for example, a disk of the patient, and the denervated portion may comprise an annulus fibrosus, a nucleus propulsus, and/or the like. Alternatively, herniation may be treated by modifying the collagen structure of the disk to strengthen the disk wall.

DETAILED DESCRIPTION OF THE INVENTION

Figure 1A:
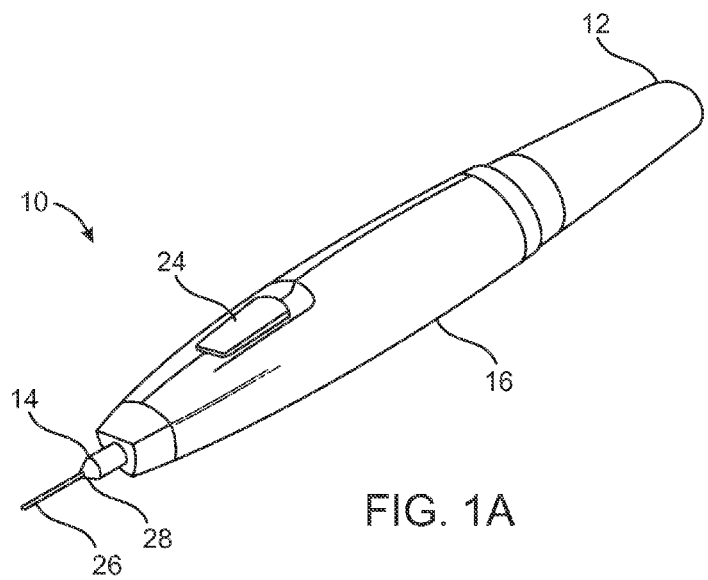
FIG. 1A is perspective view of a self-contained cryogenic pain treatment probe and system according to an embodiment of the invention.

Very generally, the present invention provides improved medical devices, systems, and methods, most often for the treatment of pain. The invention will find application in a variety of medical treatments and diagnoses, particularly for pain management of patients suffering from chronic or acute pain. Many embodiments employ cooling to remodel one or more target tissues so as to effect a desired change in a composition of the target tissue, and/or a change in its behavior. For alleviation of pain, treatments may target nerve tissue so as to interfere with the generation or transmission of sensory nerve signals associated with the pain. Other embodiments may target motor nerve tissue, muscles, neuromuscular junctions, connective tissue, or the like, so as to alleviate pain associated with contraction of a muscle.

Chronic pain that may be treated using embodiments of the invention may include (but is not limited to) lower back pain, migraine headaches, and the like. Sources of chronic pain that may be alleviated at least in part via one or more aspects of the invention may be associated with herniated disks, muscle spasm or pinched nerves (in the back or anywhere in the rest of the body), foot pain (such as plantar fascitis, plantar fibroma, neuromas, neuritis, bursitis, ingrown toenails, and the like); pain associated with malignant tumors, and the like. Applications in lower back and extremity pain may include use for patients suffering from facet joint pain syndrome, pseudosciatica, intraspinous ligament injury, superior gluteal nerve entrapment, sacroiliac joint pain, cluneal neuralgia, peripheral neuropathy, and the like.

Acute pain that may be treated using embodiments of the invention include (but is not limited to) post-surgical pain (such as pain associated with thoracotomy or inguinal hernia repair), pain associated with procedures where an epidural block, spinal block, or other regional analgesia might otherwise be employed (such as during pregnancy, labor, and delivery to inhibit pain transmission via the sensory nerves without the use of drugs), and the like. Note that the ability to manage pain without (or with less) pharmaceutical agents may allow pain relief for an extended period of time and/or when drug interactions are of concern, for example, to allow pain reduction during early labor and decrease the potential for missing the window of time when an epidural can be administered.

Cooling times, temperatures, cooling fluid vaporization pressures, cooling fluid characteristics, cooling cycle times, and/or the like may be configured to provide a desired (often a selectable) efficacy time. Treatments at moderate temperatures (for example, at temperatures which only temporarily stun tissues but do not induce significant apoptosis or necrosis) may have only short term muscle contraction or pain signal transmission inhibiting effects. Other treatments may be longer lasting, optionally being permanent. Fibroblastic response-based efficacy may, in some embodiments, be self-limiting. Probe, applicator, and/or controller designs may allow treatments with efficacy that is less dependent on operator skill, thereby potentially allowing effective treatments to be applied by persons with more limited skill and/or training through automated temperature and time control. In some embodiments, no foreign bodies and/or material need be injected into and/or left behind after treatment. Other embodiments may combine, for example, cooling with application of materials such as bioactive agents, warmed saline, or the like, to limit injury and/or enhance remodeling efficacy. Some embodiments of treatments may combine cooling with pharmaceuticals, such as a neurotoxin or the like. In some embodiments, no tissues need be removed to achieve the desired therapeutic effect, although alternative embodiments may combine cooling with tissue removal.

In many embodiments, much or all of the treatment system may be included in a single hand-held apparatus. For example, a probe body in the form of a housing may contain a sealed cooling fluid cartridge having sufficient cooling fluid for treatment of a single patient. The housing may also contain a controller and battery, with the housing often being non-sterilizable and configured for disposal so as to limit capital investment and facilitate treatments in Third-World environments.

Target tissue temperatures for temporarily disabling nerves, muscles, and associated tissues so as to provide a "stun" effect may be fairly moderate, often being in a temperature range of from about 10° C. to −5° C. Such temperatures may not permanently disable the tissue structures, and may allow the tissues to return to normal function a relatively short time after warming Using electromyographic systems, stimulation, or the like, a needle probe or other treatment device can be used to identify a target tissue, or the candidate target tissues may be cooled to a stunned temperature range to verify efficacy. In some embodiments, apoptosis may subsequently be induced using treatment temperatures from about −1° C. to about −15° C., or in some cases from about −1° C. to about −19° C. Apoptosis may optionally provide a permanent treatment that limits or avoids inflammation and mobilization of cellular repair. Colder temperatures may be applied to induce necrosis, which may be relatively long-lasting, and/or which may incite tissue healing response that eventually restores tissue function. Hence, the duration of treatment efficacy may be selected and controlled, with cooling temperatures, treatment times, and/or larger volume or selected patterns of target tissue determining the longevity of the treatment effects. Additional description of cryogenic cooling for treatment of cosmetic and other defects may be found in co-pending U.S. Pat. No. 11/295,204, filed on Dec. 5, 2005, and entitled "Subdermal Cryogenic Remodeling of Muscle, Nerves, Connective Tissue, and/or Adipose Tissue (Fat)," the full disclosure of which is incorporated herein by reference.

Figure 1B:
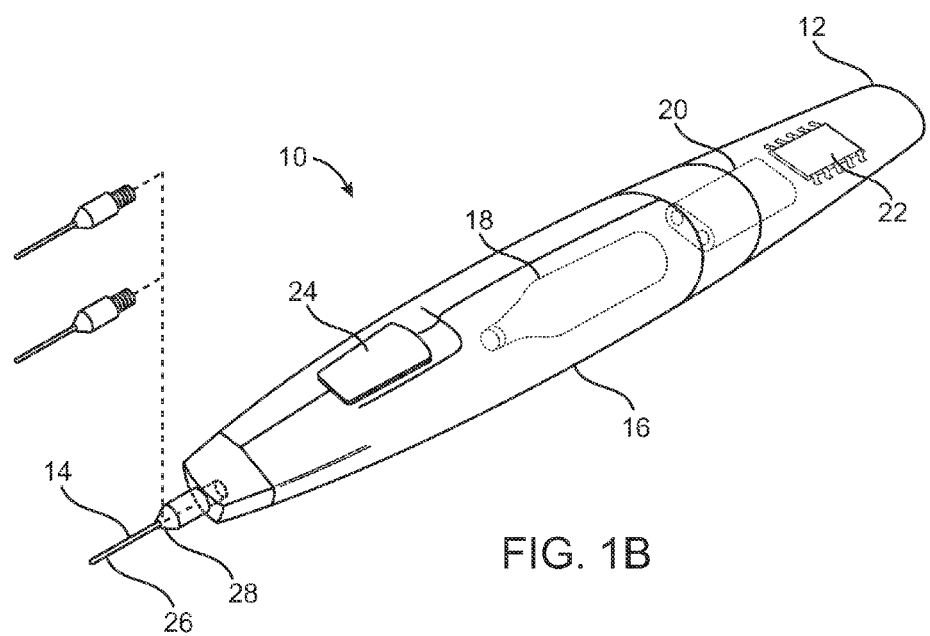
FIG. 1B is a partially transparent perspective view of the self-contained probe of FIG. 1A, showing internal components of the cryogenic remodeling system and schematically illustrating replacement treatment needles for use with the disposable probe.

Referring now to FIGS. 1A and 1B, a system for cryogenic remodeling here comprises a self-contained probe handpiece generally having a proximal end 12 and a distal end 14. A handpiece body or housing 16 has a size and shape suitable for supporting in a hand of a surgeon or other system operator. As can be seen most clearly in FIG. 1B, a cryogenic cooling fluid supply 18 and electrical power source 20 are found within housing 16, along with a circuit 22 having a processor for controlling cooling applied by self-contained system 10 in response to actuation of an input 24. Some embodiments may, at least in part, be manually activated, such as through the use of a manual supply valve and/or the like, so that processors, electrical power supplies, and the like may be absent.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 30 g needle having a sharpened distal end that is axially sealed. Probe 26 may have an axial length between distal end 14 of housing 16 and the distal end of the needle of between about ½ mm and 5 cm, preferably having a length from about 1 cm to about 3 cm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 will comprise a 16 g or smaller size needle, often comprising a 20 g needle or smaller, typically comprising a 25 g or smaller needle.

Addressing some of the components within housing 16, the exemplary cooling fluid supply 18 comprises a cartridge containing a liquid under pressure, with the liquid preferably having a boiling temperature of the less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A valve (not shown) may be disposed along the cooling fluid flow path between cartridge 18 and probe 26, or along the cooling fluid path after the probe so as to limit the temperature, time, rate of temperature change, or other cooling characteristics. The valve will often be powered electrically via power source 20, per the direction of processor 22, but may at least in part be manually powered. The exemplary power source 20 comprises a rechargeable or single-use battery.

The exemplary cooling fluid supply 18 comprises a single-use cartridge. Advantageously, the cartridge and cooling fluid therein may be stored and/or used at (or even above) room temperature. The cartridges may have a frangible seal or may be refillable, with the exemplary cartridge containing liquid $N_2O$. A variety of alternative cooling fluids might also be used, with exemplary cooling fluids including fluorocarbon refrigerants and/or carbon dioxide.

The quantity of cooling fluid contained by cartridge 18 will typically be sufficient to treat at least a significant region of a patient, but will often be less than sufficient to treat two or more patients. An exemplary liquid $N_2O$ cartridge might contain, for example, a quantity in a range from about 7 g to about 30 g of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2:
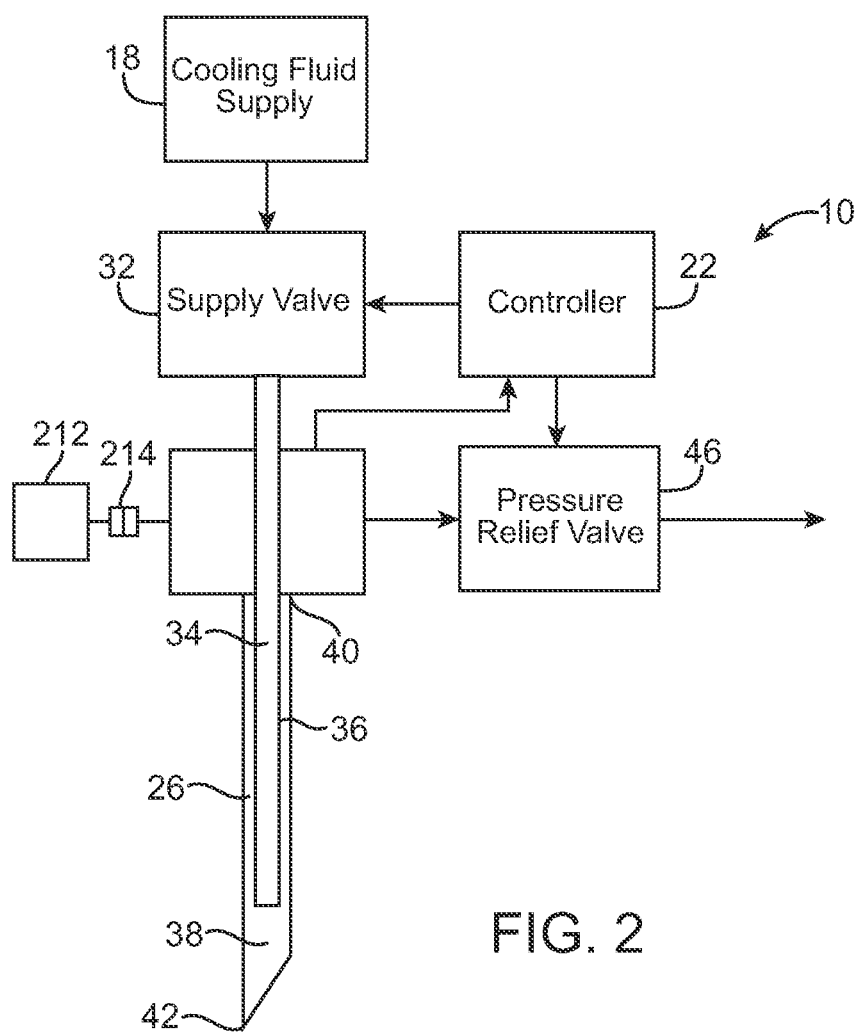
FIG. 2 schematically illustrates components that may be included in the treatment systems of FIGS. 1A and 1B.

Referring now to FIG. 2, the flow of cryogenic cooling fluid from fluid supply 18 is controlled by a supply valve 32. Supply valve may comprise an electrically actuated solenoid valve or the like operating in response to control signals from controller 22, and/or may comprise a manual valve. Exemplary supply valves may comprise structures suitable for on/off valve operation, and may provide venting of the cooling fluid path downstream of the valve when cooling flow is halted so as to limit residual cryogenic fluid vaporization and cooling. More complex flow modulating valve structures might also be used in other embodiments.

The cooling fluid from valve 32 flows through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure 36a having a polymer coating 36b (see FIG. 3A) and extends in cantilever into the needle lumen 38. Supply tube 36 may have an inner lumen with an effective inner diameter 36c of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size 36d of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−0.5 µm or tighter, as the small diameter supply tube may provide the majority of (or even substantially all of) the metering of the cooling fluid flow into needle 26.

Though supply tubes 36 having outer jackets of polyimide (or other suitable polymer materials) may bend within the surrounding needle lumen 38, the supply tube should have sufficient strength to avoid collapsing or excessive blow back during injection of cooling fluid into the needle. Polyimide coatings may also provide durability during assembly and use, and the fused silica/polymer structures can handle pressures of up to 100 kpsi. The relatively thin tubing wall and small outer size of the preferred supply tubes allows adequate space for vaporization of the nitrous oxide or other cooling fluid within the annular space between the supply tube 36 and surrounding needle lumen 38. Inadequate space for vaporization might otherwise cause a buildup of liquid in that annular space and inconsistent temperatures. Exemplary structures for use as supply tube 36 may include the flexible fused silica capillary tubing sold commercially by Polymicro Technologies, LLC of Phoenix, Ariz. under model names TSP, TSG, and TSU, optionally including model numbers TSP 020090, TSP040105, and/or others.

Figures 3, 3A:
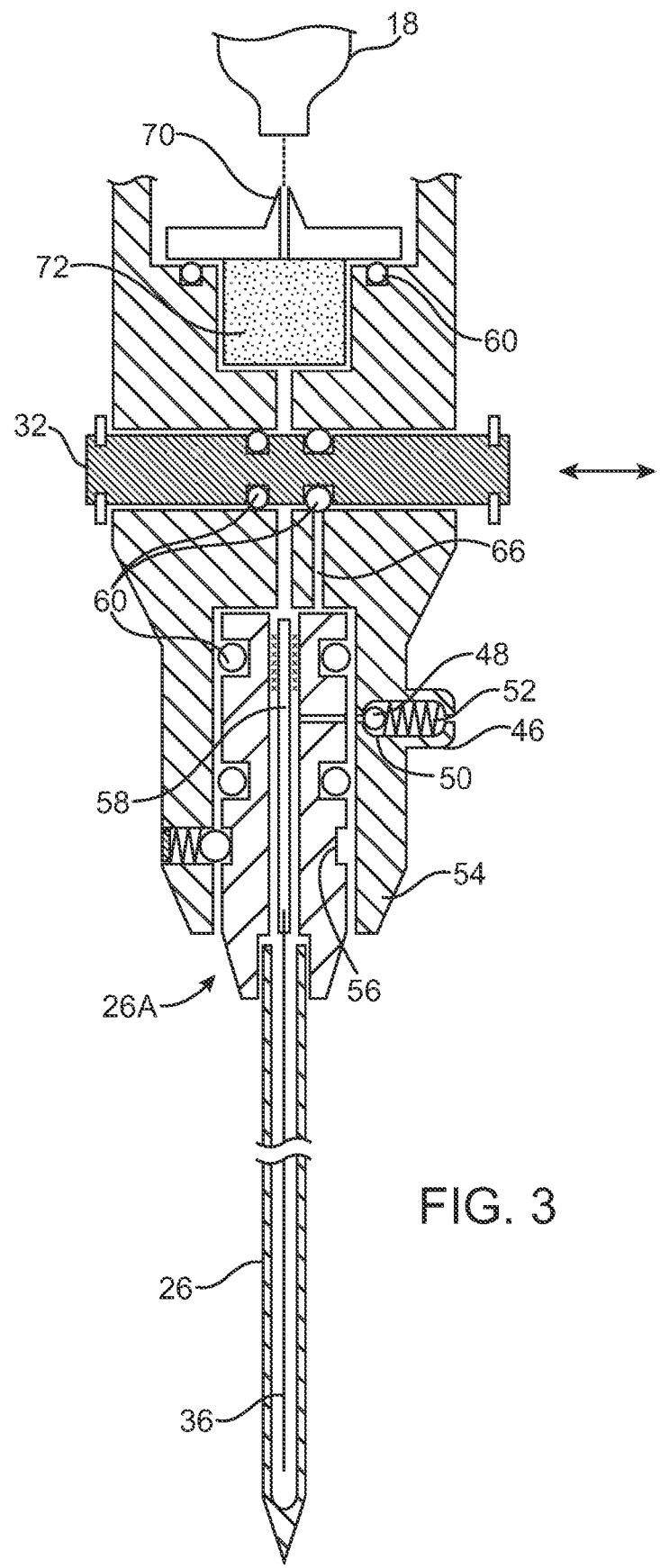
FIG. 3 is a schematic cross-sectional view of an embodiment of a distal portion of the probe in the system of FIG. 1B, showing a replaceable needle and a pressure relief valve.
FIG. 3A illustrates an exemplary fused silica cooling fluid supply tube for use in the replaceable needle of FIG. 3.

Referring now to FIGS. 2 and 3, the cooling fluid injected into lumen 38 of needle 26 will typically comprises liquid, though some gas may also be injected. At least some of the liquid vaporizes within needle 26, and the enthalpy of vaporization cools the tissue engaged by the needle. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body 48 (here in the form of a ball bearing) urged against a valve seat 50 by a biasing spring 52.

Figure 4:
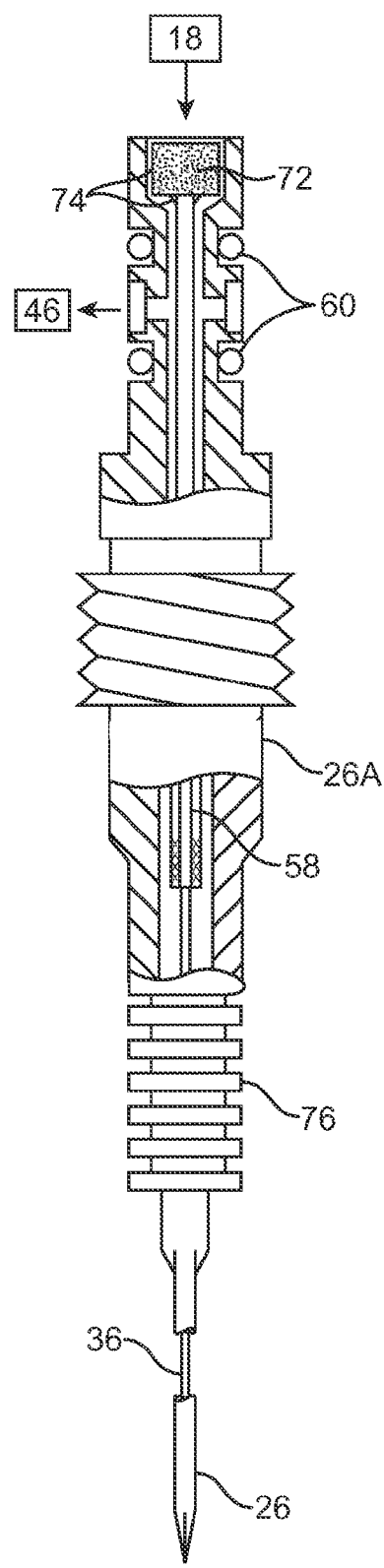
FIG. 4 is a more detailed view of a replaceable needle assembly for use in the system of FIGS. 1A and 1B.

During initiation of a cooling cycle, a large volume along the cooling fluid pathway between the exit from the supply tube and exit from the pressure relief valve 46 may cause excessive transients. In particular, a large volume in this area may result in initial temperatures that are significantly colder than a target and/or steady state temperature. This can be problematic, particularly when (for example) the target temperature is only slightly warmer than an undesirable effect inducing temperature, such as when remodeling through apoptosis or the like while seeking to inhibit necrosis. To limit such transients, the pressure relief valve 46 may be integrated into a housing 54 supporting needle 26, with the valve spring 52 being located outside the valve seat (and hence the pressure-control exit from pressure relief valve 46). Additionally, where needle 26 is included in a replaceable needle assembly 26A, pressure relief valve 46 is also located adjacent the interface between the needle assembly and probe handpiece housing 54. A detent 56 may be engaged by a spring supported catch to hold the needle assembly releasably in position, and the components of the needle assembly 26A (such as a brass or other metallic housing, a polyimide tubing 58, needle 26, and the like) may be affixed together using adhesive. Alternatively, as illustrated in FIGS. 1B and 4, the needle assembly and handpiece housing may have corresponding threads for mounting and replacement of the needle assembly. O-rings 60 can seal the cooling fluid pathway.

Additional aspects of the exemplary supply valves 32 can be understood with reference to FIGS. 2 and 3. In FIG. 3, the valve is shown in the "on" configuration, with O-rings 60 sealing either side of the cooling fluid flow path and the cooling fluid flowing around the moveable valve member. When the valve 32 is in the "off" configuration, the cooling fluid flow path downstream of the valve is vented by channel 66. Venting of the cooling fluid from the cooling fluid supply tube 36 when fluid flow is halted by supply valve 32 is advantageous to provide a rapid halt to the cooling of needle 26.

Referring now to FIGS. 3 and 4, a wide variety of alternative embodiments and refinements may be provided. Fluid supply 18 may be initially opened for use by penetrating a frangible seal of the cartridge with a pierce point 70 (such as by tightening a threaded cartridge support coupled to housing 54), with the nitrous being filtered by a filter 72 before being transmitted further along the cooling fluid path. Suitable filters may have pore sizes of from about 6 to about 25 µm, and may be available commercially from Porex of Georgia (or a variety of alternative suppliers), or may comprise a fine stainless steel screen (such as those having a mesh size of 635 with 0.0009" wire and spacing between the wire edges of approximately 0.0006"), or the like. A wide variety of epoxy or other adhesives 74 may be used, and the replaceable needle housing 24A and other structural components may comprise a wide variety of metals or polymers, including brass or the like. Fins 76 may be included to help vaporize excess cooling liquid traveling proximally of the insertable length of needle 26.

Very fine needles will typically be used to deliver to cooling at and/or below the surface of the skin. These needles can be damaged relatively easily if they strike a bone, or may otherwise be damaged or deformed before or during use. Fine needles will help inhibit damage to the skin during insertion, but may not be suitable for repeated insertion for treatment of numerous treatment sites or lesions of a particular patient, or for sequential treatment of a large area of the patient. Hence, the structures shown in FIGS. 1B, 3, and 4 allow the use of probe bodies 16, 54 with a plurality of sequentially replaceable needles. O-rings 60 help to isolate the cooling fluid supply flow (which may be at pressures of up to about 900 psi) from the exhaust gas (which may be at a controlled pressure in a range between about 50 and 400 psi, depending on the desired temperature). Exemplary O-rings may comprise hydrogenated Buna-N O-rings, or the like.

Figure 5:
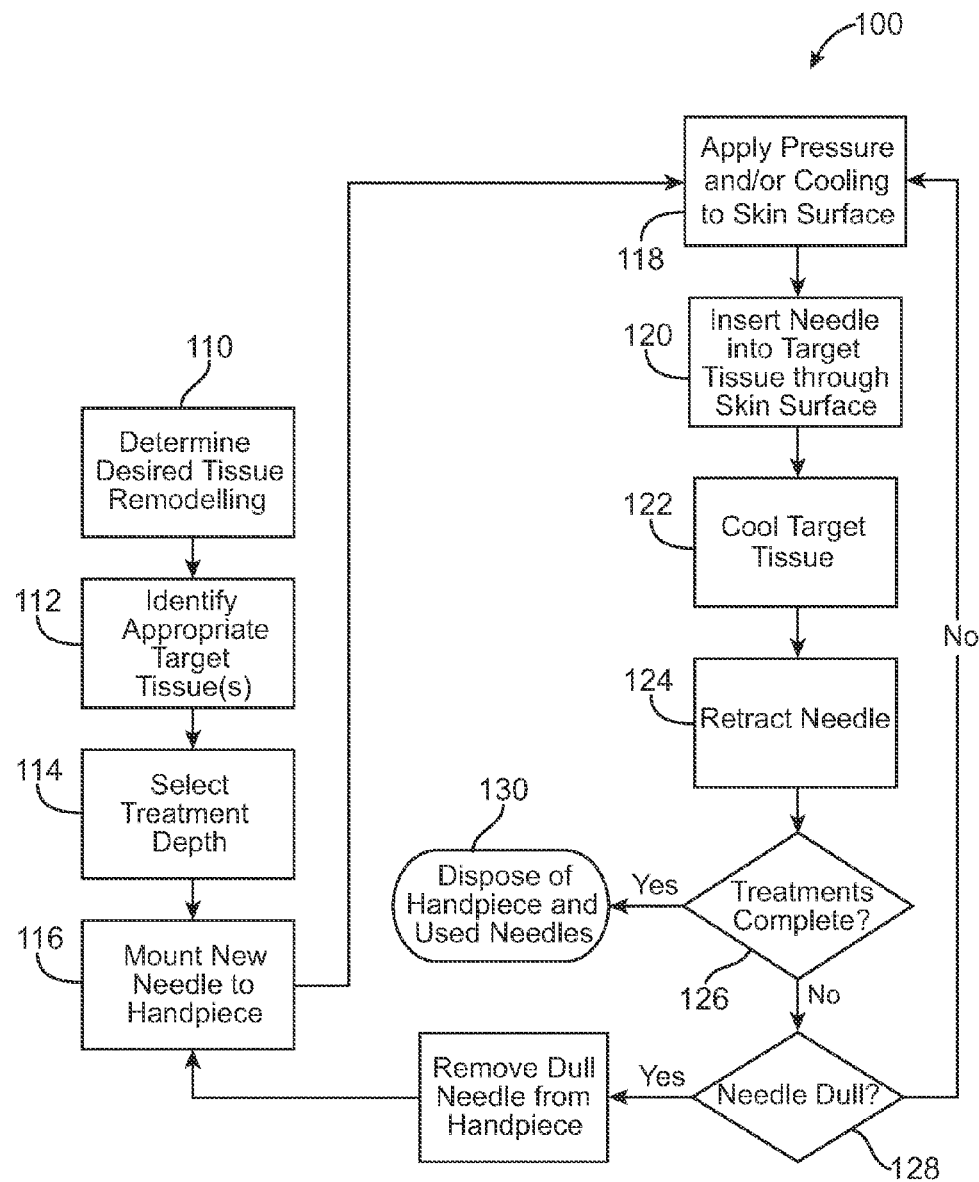
FIG. 5 is a flowchart schematically illustrating a method for treatment using the disposable cryogenic probe and system of FIG. 1B.

Referring now to FIG. 5, a method 100 facilitates treating a patient using a cryogenic cooling system having a self-contained disposable handpiece and replaceable needles such as those of FIG. 1B. Method 100 generally begins with a determination 110 of the desired tissue remodeling and results, such as the alleviation of specific cosmetic wrinkles of the face, the inhibition of pain from a particular site, the alleviation of unsightly skin lesions or cosmetic defects from a region of the face, or the like. Appropriate target tissues for treatment are identified 112 (such as the subdermal muscles that induce the wrinkles, a tissue that transmits the pain signal, or the lesion-inducing infected tissues), allowing a target treatment depth, target treatment temperature profile, or the like to be determined 114. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, cooling, or both may be applied 118 to the skin surface adjacent the needle insertion site before, during, and/or after insertion 120 and cryogenic cooling 122 of the needle and associated target tissue. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply cartridge included in the self-contained handpiece is depleted, the used handpiece and needles can be disposed of 130.

A variety of target treatment temperatures, times, and cycles may be applied to differing target tissues to as to achieve the desired remodeling. For example, (as more fully described in patent application Ser. No. 11/295,204, previously incorporated herein by reference) desired temperature ranges to temporarily and/or permanently disable muscle, as well as protect the skin and surrounding tissues, may be indicated by Table II as follows:

TABLE II

| Temperature | Skin | Muscle/Fat |
|---|---|---|
| 37° C. | baseline | baseline |
| 25° C. | cold sensation | |
| 18° C. | reflex vasodilation of deep blood vessels | |
| 15° C. | cold pain sensation | |
| 12° C. | reduction of spasticity | |
| 10° C. | very cold sensation reduction of chronic oedema Hunting response | |
| 5° C. | pain sensation | |
| 0° C. | freezing point | |
| −1° C. | | Phase transition begins |
| −2° C. | | minimal apoptosis |
| −3° C. | | Peak phase transition |
| −5° C. | tissue damage | moderate apoptosis |
| −8° C. | | Completion of phase transition |
| −10° C. | | considerable apoptosis |
| −15° C. | | extensive apoptosis mild-moderate necrosis |
| −19° C. | | adoptosis in some skeletal muscle tissues |
| −40° C. | | extensive necrosis |

To provide tissue remodeling with a desired or selected efficacy duration, tissue treatment temperatures may be employed per Table III as follows:

TABLE III

| Cooled Temperature Range | Time Effectiveness | Purpose |
|---|---|---|
| ≥0° C. | Treatment lasts only while the needle is inserted into the target tissue. | Can be used to identify target tissues. |
| From 0° C. to −5° C. | Often lasts days or weeks, and target tissue can repair itself. Embodiments may last hours or days. | Temporary treatment. Can be used to evaluate effectiveness of remodeling treatment on skin surface shape or the like. |
| From −5° C. to −15° C. | Often lasts months to years; and may be permanent. Limited muscle repair. Embodiments may last weeks to months. | Long term, potentially permanent cosmetic benefits. Can be deployed in limited doses over to time to achieve staged impact, controlling outcome and avoiding negative outcome. May be employed as the standard treatment. |

TABLE III-continued

| Cooled Temperature Range | Time Effectiveness | Purpose |
| --- | --- | --- |
| From −15° C. to −25° C. | Often lasts weeks or months. Muscle may repair itself via satellite cell mobilization. Embodiments may last years. | May result in Mid-term cosmetic benefits, and can be used where permanent effects are not desired or to evaluate outcomes of potentially permanent dosing. Embodiments may provide permanent treatment. |

There is a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of these apoptosis and necrosis may also provide long-lasting or permanent benefits. For the reduction of adipose tissue, a permanent effect may be advantageous. Surprisingly, both apoptosis and necrosis may produce long-term or even permanent results in adipose tissues, since fat cells regenerate differently than muscle cells.

Figure 6:
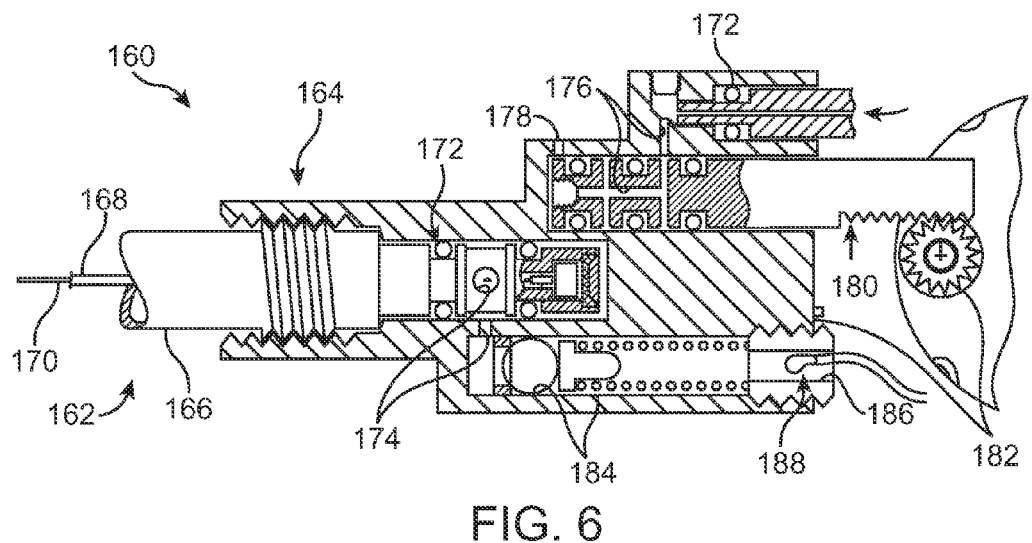
FIG. 6 is a schematic cross-sectional view showing an alternative exemplary needle interface, along with adjacent structures of the needle assembly and probe body.

Referring now to FIG. 6, an exemplary interface 160 between a cryogenic cooling needle probe 162 and the associated probe body structure 164 are illustrated, along with adjacent portions of the needle, valve, probe body, and the like. Needle probe 162 is included in a needle assembly having a needle hub 166 with a lumen containing a polyimide tube 168 around a fused silica cooling fluid supply tube with its polyimide jacket 170. O-rings 172 seal in exhaust gas path 174 and inlet cooling fluid path 176, with the inlet path having a vent 178 to minimize run-on cooling when the cooling fluid supply is shut off by a valve 180, as generally described above. The valve is here actuated by a motor 182, while the exhaust gas pressure is controlled using a biasing spring and ball valve 184 as described above. A hollow set screw 186 can be used to assemble and/or adjust the pressure relief valve, and a thermistor 188 can be used to sense cooling gas flow.

Figure 7:
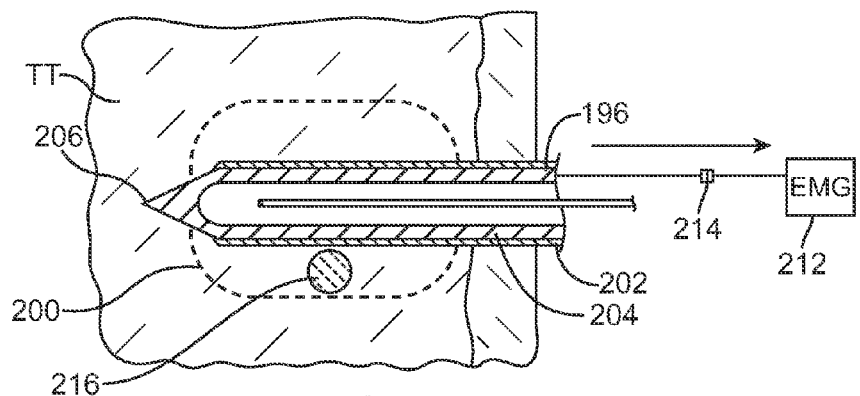
FIG. 7 is a partial cross-sectional view schematically illustrating a cryogenic treatment probe in which cooling is performed at least in part through an insulating surface, and having an electrically conductive surface for coupling to an electromyographic system to facilitate locating a nerve.

Referring now to FIG. 7, cryogenic cooling probe 196 is inserted into a target tissue TT and a flow of cryogenic cooling fluid is injected into the needle as generally described above. A region 200 of target tissue TT is cooled sufficiently to freeze and effect the desired remodeling of at least a portion of the target tissue. Rather than waiting for the frozen tissue to thaw, in the embodiment of FIG. 7 a lubricious coating 202 facilitates removal of the needle while at least a portion of the target tissue remains frozen. The lubricious coating may comprise a material having a thermal conductivity which is significantly less than that of the underlying probe structure 204. Coating 202 may have a thickness which is significantly less than that of the underlying probe structure 204, limiting the total thermal insulation effect of the coating, and/or an internal temperature of probe 196 may be reduced so as to provide the overall cooling treatment. Note that a small surface 206 of probe 196 may be free of lubricious coating 202. Where the underlying probe structure 204 comprises an electrical conductor such as stainless steel (or some alternative metal), and where coating 202 comprises an electrical insulator, the uncovered portion 206 may be used as an electrode for neurostimulation during positioning of probe 196 or the like. Additionally, an EMG system 212 may be coupled to the electrically conductive surface 206 via a coupler 214 (see FIG. 2). Coupler 214 will typically be accessible from the exposed probe body when needle 26 is inserted into the patient, and EMG system 212 may be used for identifying and/or verifying the location of nerve 216 during and/or after insertion of needle 196, depending on the configuration of the conductive surface 206 and the like.

Figure 8:
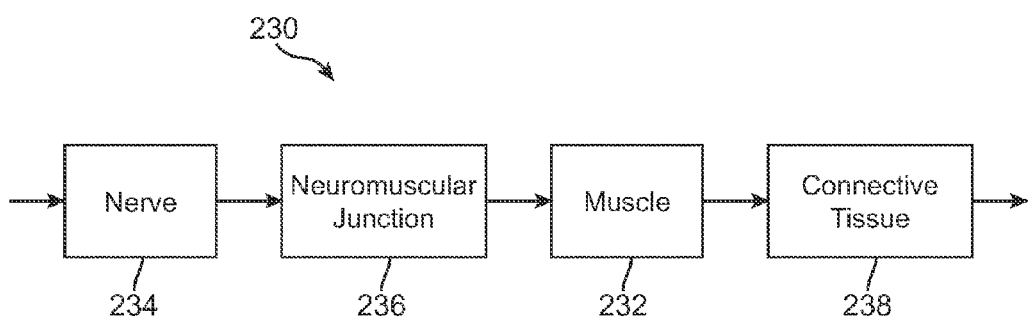
FIG. 8 is a block diagram schematically illustrating tissue components included in a contractile chain.

Referring now to FIG. 8, in some embodiments remodeling of the tissue may inhibit contraction of a muscle so as to mitigate pain associated with contraction or spasm. Remodeling a tissue included in a contractile function chain 230 may be used to effect a desired change in the composition of the treated tissue and/or a change in its behavior that is sufficient to alleviate the pain. While this may involve a treatment of the tissues of muscle 232 directly, treatments may also target nerve tissues 234, neuromuscular junction tissues 236, connective tissues 238, and the like. Still further tissues may directly receive the treatment, for example, with treatments being directed to tissues of selected blood vessels so as to induce hypoxia in muscle 232 or the like. Regardless of the specific component of contractile chain 230 which is treated, the treatment will preferably inhibit contraction of muscle 232 which would otherwise induce pain.

Figure 9A:
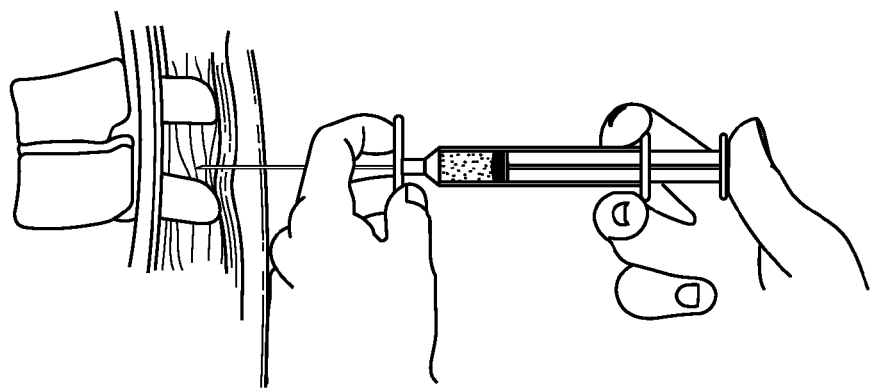
FIGS. 9A-9C illustrate a method for positioning a pain treatment probe in an epidural space.
Figure 9B:
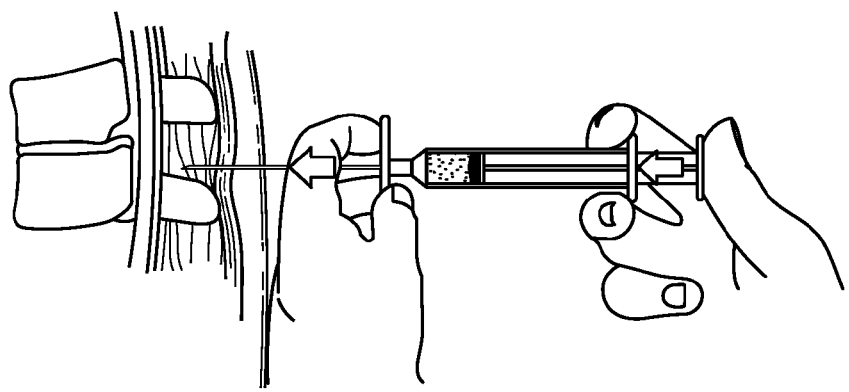
Figure 9C:
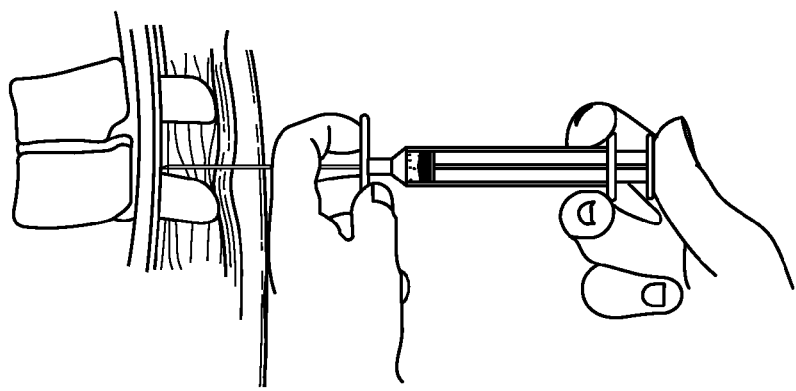

Referring now to FIGS. 9A-C, techniques known for accessing the epidural space for introduction of pain-inhibiting compounds may be adapted for positioning cooling needles similar to those described herein. By providing a needle with a through-lumen having an open distal port near the end of the needle, saline or other fluids can be injected during needle insertion and positioning. Resistance of the needle to insertion and/or a change in injection resistance indicates the port may be disposed in the epidural space. The through-lumen may be disposed on the cooling needle concentrically or eccentrically relative to the cooling fluid supply path and/or the exhaust fluid path. A hypodermic syringe (or the like) used to provide fluid to the through lumen may then be replaced by a body containing or coupled to a cryogenic fluid cooling source, as can be understood with reference to FIGS. 1B, 3, and 4. Alternatively, a separate needle having a through-lumen may be used as a guide for insertion of the cooling needle, such as by advancing the cooling needle through the through-lumen or the like.

Figure 10:
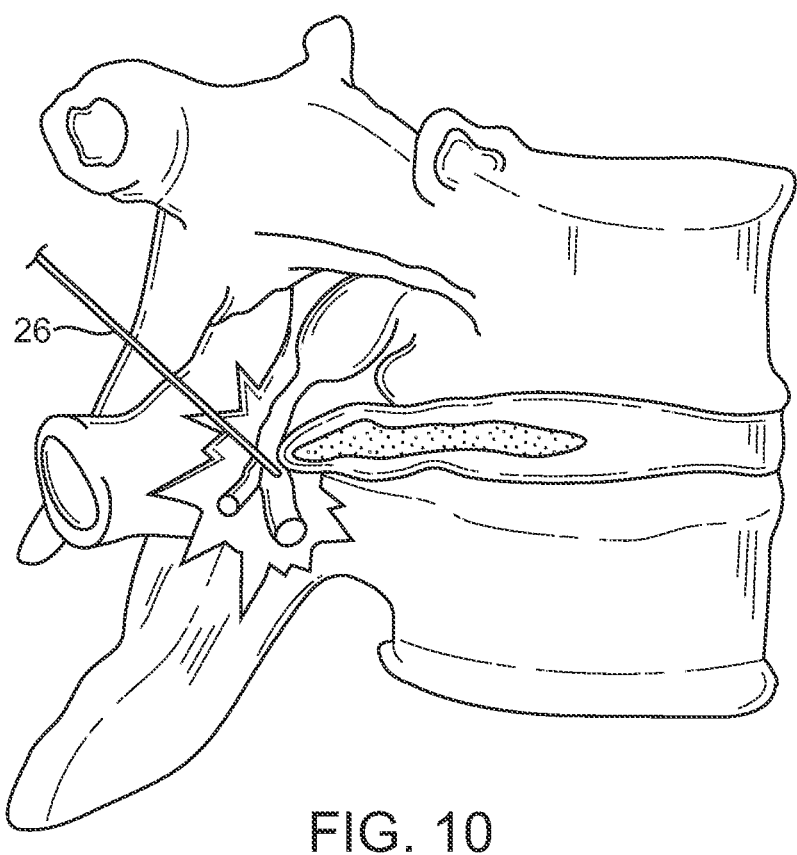
FIG. 10 illustrates component tissues of a spine and treatment of those tissues with a cooling probe.

As can be understood with reference to FIG. 10, the cooling needle 26 may be thermally coupled to a target nerve by positioning the needle in proximity to a spinal cord adjacent the epidural space, to a branch nerve from the spinal column in or adjacent a vertebral foramen to a herniated disk, or to another target neural and/or spinal tissue. Verification of positioning may be provided using an electro-myographic system (EMG) as described above, and/or positioning may optionally be guided using fluoroscopy, ultrasound imaging, magnetic resonance imaging (MRI), and/or other imaging modalities.

While exemplary embodiments have been described in some detail for clarity of understanding and by way of example, a number of modifications, changes, and adaptations may be implemented and/or will be obvious to those as skilled in the art. Hence, the scope of the present invention is limited solely by the independent claims.

What is claimed is:

1. A method for treating pain associated with a nerve of a patient, the nerve underlying a skin surface, the method comprising:
    manually manipulating a body with a hand, the body supporting a needle, the body manipulated so as to advance a distal end of the needle through the skin surface to thermally couple the needle with the nerve, wherein the needle has a needle size of 25 gauge or smaller and has a lumen extending distally toward the distal end, wherein a cooling fluid supply tube extends distally within the lumen of the needle, and wherein the manipulating of the body is performed so that the cooling fluid supply tube extends distally of the skin surface; and
    transmitting cooling fluid from a cooling fluid source to the fluid supply tube within the needle so that the fluid flows through the fluid supply tube distally of the skin surface and cools the needle, and so that the needle cools the nerve sufficiently that the pain is inhibited.

2. The method of claim 1, wherein the cooling fluid comprises a cryogenic cooling fluid and further comprising vaporizing at least a portion of the cryogenic cooling fluid within the lumen of the needle so that enthalpy of vaporization cools a tissue region of the patient to a temperature in desired range so as to interfere with pain signal transmission along the nerve, the nerve comprising a sensory nerve and extending within the region.

3. The method of claim 2, wherein the region is separated from and disposed distally of the skin surface.

4. The method of claim 2, wherein the cooling fluid comprises $N_2O$.

5. The method of claim 4, wherein the cooling fluid supply comprises a cartridge supported by the body, and wherein the cartridge contains a quantity of liquid $N_2O$ sufficient for cooling a plurality of tissue regions of the patient, and further comprising storing the liquid $N_2O$ in the cartridge at room temperature.

6. The method of claim 2, further comprising removing the needle from the body and mounting another needle to the body, manually manipulating the body so as to advance the distal end of the other needle through the skin; and
    transmitting cooling fluid from the cooling fluid source to another fluid supply tube within the other needle, and vaporizing at least a portion of the cryogenic cooling fluid within the lumen of the other needle so as to cool another tissue region of the patient to a temperature in the desired range.

7. The method of claim 6, wherein the size of the needle is 26 gauge or smaller.

8. The method of claim 2, wherein the cooling fluid supply tube within the needle has an outer diameter in a range between about 60 and 150 micrometers.

9. The method of claim 2, wherein the cooling of the nerve within the region to the temperature is sufficient to induce long-term inhibition of pain signal transmission along the nerve.

10. The method of claim 9, wherein the temperature is less than −19 C. and the cooling of the nerve does not induce permanent inhibition of signal transmission along the nerve.

11. The method of claim 9, wherein the cooling of the nerve inhibits the pain signal transmission for months or years.

12. The method of claim 9, wherein the pain comprises chronic foot pain.

13. The method of claim 9, wherein the pain comprises extremity pain.

14. The method of claim 9, wherein the pain comprises back pain.

15. The method of claim 1, further comprising identifying the nerve using an electrically conductive surface of the needle.

16. The method of claim 1, further comprising verifying a location of the nerve using an electrically conductive surface of the needle.

17. A system for treating pain associated with a nerve of a patient, the nerve underlying a skin surface tissue, the system comprising:
    a needle having a distal end and a needle size of 25 gauge or smaller, the needle having a lumen extending distally toward the distal end;
    a body having an interface, the interface removably receiving the needle, the body having a handle configured for manually manipulating with a hand when the needle is on the interface so as to advance the distal end of the needle through the skin surface and into the tissue to an inserted position, the needle being thermally coupled with the nerve in the inserted position; and
    a cooling fluid supply tube extending distally within the lumen of the needle such that the cooling fluid supply tube extends distally of the skin surface when the needle is in the inserted position, the cooling fluid supply tube coupleable with a cooling fluid source so that cooling fluid flows from the source through the fluid supply tube distally of the skin surface and cools the needle, and so that the needle cools the nerve sufficiently that the pain is inhibited.

18. The system of claim 17, the nerve comprising a sensory nerve and extending within a tissue region of the patient, wherein the cooling fluid comprises a cryogenic cooling fluid, wherein the cooling fluid supply tube and the lumen of the needle are included in a cooling fluid flow path configured so that at least a portion of the cooling fluid vaporizes within the lumen of the needle, when the needle is in the inserted position within the tissue region and the cooling fluid flows along the cooling fluid path, such that enthalpy of vaporization cools the tissue region to a temperature in desired range to interfere with pain signal transmission along the nerve.

19. The system of claim 18, wherein the needle and cooling fluid supply tube are configured so that region is separated from and disposed distally of the skin surface.

20. The system of claim 18, further comprising the cooling fluid supply, the cooling fluid comprising $N_2O$.

21. The system of claim 18, wherein the cooling fluid supply comprises a cartridge supported by the body, and wherein the cartridge contains a quantity of liquid $N_2O$ sufficient for cooling a plurality of tissue regions of the patient and is configured for storage of the liquid $N_2O$ in the cartridge at room temperature.

22. The system of claim 21, further comprising a plurality of needles, each of the needles having an associated needle size of 25 gauge or smaller and removably receivable by the interface so as to facilitate sequentially removal and replacement of the needles on the body, each of the needles having an associated distal end, a lumen extending toward the distal end, and a cooling fluid supply tube, the body configured to sequentially transmit portions of the quantity of the cooling fluid from the cooling fluid source to the fluid supply tube associated with the needle received by the interface of the body so that at least a portion of the cryogenic cooling fluid vaporizes within the associated lumen of the receive needle so as to cool an associated tissue region of the patient to a temperature in the desired range.

23. The system of claim 22, wherein the size of the needles is 26 gauge or smaller.

24. The system of claim 23, wherein the cooling fluid supply tube within each needle has an outer diameter in a range between about 60 and 150 micrometers.

25. The system of claim 18, wherein the temperature is sufficient to induce long-term inhibition of pain signal transmission along the nerve.

26. The system of claim 25, wherein the temperature is less than −19 C.

27. The system of claim 17 wherein the needle has an electrically conductive surface coupled with an electrical connector, the connector configured for interfacing with a system configured for verifying a location of the nerve using the conductive surface.

28. The system of claim 27 wherein the nerve location verification system comprises an electromyographic system.

29. The system of claim 27 wherein the nerve location verification system comprises a nerve stimulation system.

30. The system of claim 17, wherein the distal end of the needle comprises a sharpened distal end configured to penetrate the skin surface.

* * * * *